United States Patent [19]

Wakatake

[11] Patent Number: 5,318,359

[45] Date of Patent: Jun. 7, 1994

[54] AUTOMATIC MEDICAL SAMPLING DEVICE

[75] Inventor: Koichi Wakatake, Tokyo, Japan

[73] Assignee: Kabushiki Kaisha Nittec, Tokyo, Japan

[21] Appl. No.: 961,198

[22] Filed: Oct. 14, 1992

Related U.S. Application Data

[60] Continuation of Ser. No. 647,897, Jan. 30, 1991, abandoned, which is a division of Ser. No. 437,221, Nov. 16, 1989, Pat. No. 5,132,088.

[30] Foreign Application Priority Data

| Nov. 17, 1988 | [JP] | Japan | 63-150131 |
| Jul. 18, 1989 | [JP] | Japan | 1-083566 |
| Oct. 20, 1989 | [JP] | Japan | 1-122199 |
| Oct. 20, 1989 | [JP] | Japan | 1-122200 |
| Oct. 20, 1989 | [JP] | Japan | 1-122201 |

[51] Int. Cl.$^5$ ............... B01F 15/02; B01F 9/00; B01L 11/00
[52] U.S. Cl. ............. 366/140; 366/184; 366/197; 366/220; 366/235; 422/100
[58] Field of Search ........ 366/220, 233, 234, 235, 366/237, 213, 214, 204, 199, 200, 197, 251, 198, 222, 224, 54, 62, 63, 219, 602, 605, 184, 140; 494/16, 17, 18, 19; 422/61, 63, 99, 64, 72, 100, 258, 259, 101, 102, 104, 297, 270; 192/66; 403/166, 109, 108; 435/312; 74/470

[56] References Cited

U.S. PATENT DOCUMENTS

| 1,804,707 | 5/1931 | Rudin | 366/224 |
| 2,317,559 | 4/1943 | Stout | 366/220 |
| 3,206,999 | 9/1965 | Roth | 403/166 |
| 3,860,102 | 1/1975 | Hosemann | 192/66 |
| 3,935,884 | 2/1976 | Hazelton | 366/219 |
| 4,104,831 | 8/1978 | Kobayashi | 494/19 |
| 4,299,500 | 11/1981 | Bassetti | 366/198 |
| 4,447,395 | 5/1984 | Englar et al. | 422/104 |
| 4,680,164 | 7/1987 | Kelln | 422/72 |
| 4,729,778 | 3/1988 | Griffin | 422/104 |
| 4,848,917 | 7/1989 | Benin et al. | 366/110 |
| 4,911,847 | 3/1990 | Schmidt et al. | 422/101 |
| 5,005,981 | 4/1991 | Schulte et al. | 494/15 |

FOREIGN PATENT DOCUMENTS

1080072 4/1960 Fed. Rep. of Germany ...... 366/220

Primary Examiner—Harvey C. Hornsby
Assistant Examiner—Tony G. Soohoo
Attorney, Agent, or Firm—Lowe, Price, LeBlanc & Becker

[57] ABSTRACT

An automatic medical sampling device comprises a vacuum breaking needle for connecting the inside of a vacuum blood gathering tube with the air. An inserting needle has a length sufficient to be located at a position slightly below the lower end of the vacuum breaking needle at the highest position of the vacuum breaking needle. A container holder or maintainer has a bottom slope or projections for supporting a container, and a stirring device stops reciprocation of the stirring bar by detecting the position of the bar.

2 Claims, 8 Drawing Sheets

AUTOMATIC MEDICAL SAMPLING DEVICE

This application is a continuation of application Ser. No. 07/647,897 filed Jan. 30, 1991, now abandoned, which is a division of application Ser. No. 07/437,221, filed Nov. 16, 1989, now U.S. Pat. No. 5,132,088, issued Jul. 21, 1992.

FIELD OF THE INVENTION

This invention relates generally to an automatic medical sampling device and more particularly, to a device which is set in a blood corpuscle calculation device, etc., and can prevent a vacuum breaking needle, which makes the pressure inside a vacuous blood gathering tube equal to atmosphere pressure, from being closed by clinging blood. The invention also relates to a container holder and maintainer in an automatic medical sampling device which can support containers of blood samples etc. therein. The invention further relates to a stirring device for an automatic medical sampling device which rotates containers for blood samples etc. therein, stirs and mixes the samples.

BACKGROUND OF THE INVENTION

A vacuous blood gathering tube has been frequently used as a device to gather blood easily, and when gathering blood using the vacuous blood gathering tube, it often happens that pressure inside of the blood gathering tube is less than the pressure of air even after gathering blood. When used in a blood corpuscle calculation device etc., for example, a vacuous blood gathering tube in such a condition results in the following problems.

A pipette provided in a blood corpuscle calculation device etc., is generally filled with wash water. Accordingly, when a certain amount of blood is absorbed from the vacuous blood gathering tube by the pipette, there is a problem that the wash water is absorbed into the vacuous blood gathering tube, since pressure inside of the vacuous blood gathering tube is less than pressure of air, diluting the blood. This problem is of a sufficient degree that the absorbing power of an absorbing pump is reduced remarkably, and absorbing of blood becomes inadequate.

As a means to solve these problems, the applicant previously has suggested an automatic medical sampling device which releases air inside of the vacuous blood gathering tube, using a vacuum breaking needle. This automatic sampling device is constituted as follows. Pressure inside the vacuous blood gathering tube is made equal to the pressure of air by sticking vacuum breaking needle through the stopper of the vacuous blood gathering tube, while blood is absorbed by the pipette as ever.

However, in the means to release air using the vacuum breaking needle, blood frequently clings to the side of a stopper applied on the vacuous blood gathering tube. Therefore whenever penetrating the stopper by the vacuum breaking needle, blood accumulates in the needle and blocks the inside of the vacuum breaking needle preventing pressure equalization. This problem happens as well when releasing air inside of the vacuous blood gathering tube by the pipette.

In a previous stirring device, apparatus for mixing and stirring samples by rotating a stirring bar soaked in the samples, and for mixing and stirring by rotating and shaking the container, or for mixing and stirring the sample by rotating the stirring bar in contact with the top of the container of the sample therein, are known. However, in the former type of soaking and stirring, there is a problem that since a washing mechanism for washing the stirring bar after stirring is necessary, the apparatus becomes very complicated and expensive. Furthermore, if washing the stirring bar is not complete, harmful influence by the previous sample (cross contamination) is apt to happen.

As a means to solve such a problem, the latter type of non-contact stirring has been sometimes used. With previous type of revolving and stirring apparatus requiring rotating, shaking and stirring the container, after stirring has been finished, the container has to be reset in the sampling device, etc. Accordingly, such an operation is complicated and inefficient. In the contact type of device for rotating the stirring bar, wherein there is contact with the top of the container, there is a problem as follows.

In the above type of stirring, the size (length, width) of the container used varies. Accordingly, there is a problem that the stirring bar, having a certain down stroke, is not in contact with the container. There is also a possibility that the container will be broken by excessive contact pressure. If the container is not broken, when stirring is done by positioning the stirring bar in a container holder, stirring is carried out under the condition that the inside diameter of container receiving holes of the container holder is not equal to the outside diameter of each container. Accordingly, strange sounds occur and an effective stirring is not obtained. Furthermore, recently, while rotating the container, an automatic analysis device has been used that reads, at high speeds, bar code information applied on the container scanning the bar code reading device. Accordingly, if the container is rotated with the container inclined inside the holes, the bar code information cannot be read during stirring.

SUMMARY OF THE INVENTION

Accordingly, it is an object of the invention to provide an automatic medical sampling device in which clinging of blood in a vacuum breaking needle used to release air inside of a vacuous blood gathering tube can be prevented.

It is a further object of the invention to provide an automatic medical sampling device in which, when absorbing blood from a vacuous blood gathering tube, air inside the tube can be released at the same time safely and easily, and by absorbing blood and releasing air from vacuous blood gathering tubes positioned in the blood gathering tube holder, inadvertent absorbing of blood can be prevented.

It is a further object of the invention to provide a container holder and maintainer for an automatic medical sampling device in which, when standing the container in receiving holes in the container holder, and rotating the holder and stirring by a non-contact stirring bar, containers of different sizes can be positioned vertically along the axes of the receiving holes.

It is a further object of the invention to provide a stirring device for an automatic medical sampling device in which, in a type of stirring device for stirring samples without soaking a stirring portion of the device, containers of different lengths can always push a stirring bar at a proper pressure and rotate the stirring bar and the containers in the best condition.

According to the invention, an automatic medical sampling device is made as follows. In an automatic sampling device to transfer a vacuous blood gathering tube blood therein to a position for absorbing blood in sequence, a vacuum breaking needle used to pass air into a vacuous blood gathering tube is positioned to be able to rise to an upper position for absorbing blood. An inserting needle is inserted in an air passage of the vacuum breaking needle, and has a length such that the lowest portion thereof is located below the vacuum breaking needle when the needle is located at its highest position.

The automatic medical sampling device has a blood gathering tube holder to support a vacuous blood gathering tube blood therein, an axis to rotate the blood gathering tube holder from a position for inserting the tube to a position for absorbing blood, a pipette to absorb blood from the vacuous blood gathering tube at a blood absorbing position, a vacuum breaking needle positioned near the pipette to pass air in the vacuous blood gathering tube, a reciprocating device to index the pipette and the vacuum breaking needle up and down, an inserting needle to be inserted in the vacuum breaking needle, and a washing device to wash the pipette following a blood absorbing operation.

The automatic medical sampling device preferably has a container holder in the form of receiving holes. The lower end of each hole has a cone-shaped slope or a certain number of projections to support containers along the axes of the holes in the container holder.

The automatic medical sampling device further preferably has a container maintainer to position a container located in the holes in the container holder along the hole axes thereof. The maintainer is made of a maintainer section having an outside diameter sufficient to contact the inside surfaces of the receiving holes, and a maintaining hole formed in the maintainer section positions the container along the axis of the receiving hole. The bottom of each maintaining hole has a cone-shaped slope.

The automatic medical sampling device additionally preferably has a container maintainer which is made of a maintainer section having an outside diameter sufficient to contact the inside surfaces of a receiving hole, and the lower ends of maintaining holes in the maintainer section each has a certain number of projections to position a container along the axis of each of the receiving holes.

The automatic medical sampling device furthermore preferably has a stirring device which comprises a stirring bar to be pushed against the top of a container, an elongated groove in the top portion of the stirring bar, a motor axis for stirring having a projection to reciprocate in the groove, a motor for rotating the stirring bar to rotate the motor axis, a spring to nomally push the stirring bar downward, a holder to hold the motor for rotating the stirring bar and to hold the stirring bar, a stirring bar reciprocating device to index the holder between upper and lower positions, and a pressure sensor in the holder to control rotation of the stirring bar. The pressure sensor detects the position of the stirring bar falling by the device to reciprocate the stirring bar and in response stops driving the device.

BRIEF DESCRIPTION OF THE DRAWINGS

The invention will be explained in more detail in conjunction with appended drawings, wherein.

DESCRIPTION OF THE PREFERRED EMBODIMENT

Figure 1:
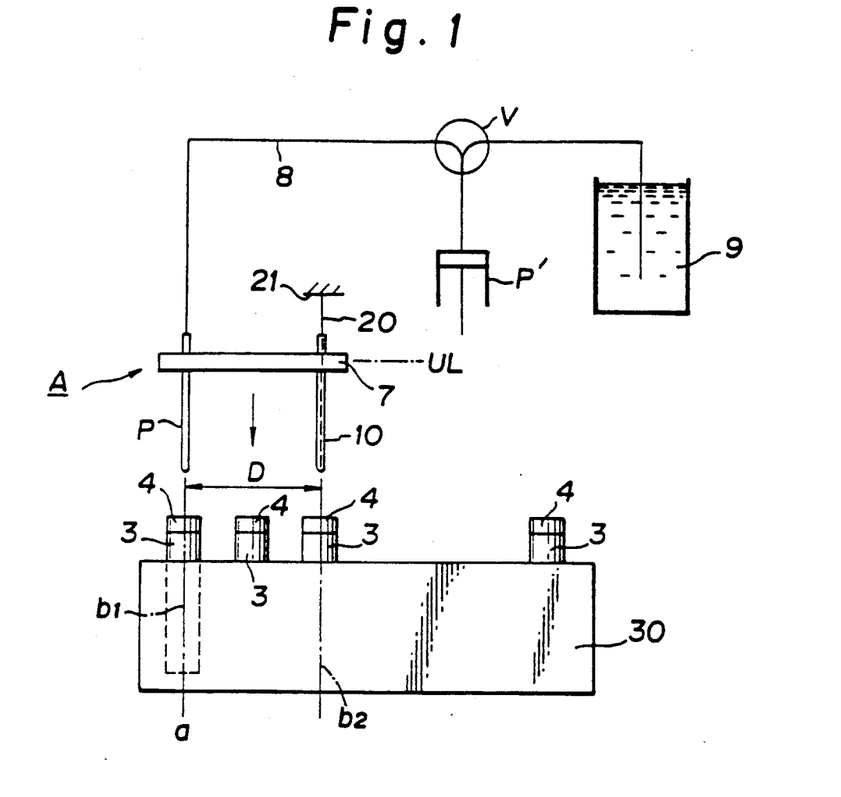
FIG. 1 is a schematic view to show a whole structure of of the automatic medical sampling device to explain a first preferred embodiment of the invention.

As shown in FIG. 1, FIG. 2, FIG. 6, and FIG. 7, an automatic medical sampling device A in this preferred embodiment comprises a holder 30 to position plural vacuous blood gathering tubes 3, a holder transferring device (not shown) to transfer intermittently and at a certain timing the vacuous blood gathering tubes 3 to the position where a pipette p indexes downward, a device (not shown) to control reciprocation of pipette p at the position where the pipette falls, a vacuum breaking needle 10 fixed in a pipette holder 7 of the pipette, and an inserting needle 20 to be inserted in the vacuum breaking needle 10, as shown in the FIG. 1.

The vacuous blood gathering tube 3 is made as usual. A stopper 4 is set on the upper portion thereof and seals up the vacuous blood gathering tube 3.

The holder 30 to position the plural vacuous blood gathering tubes 3 transfers the vacuous blood gathering tubes 3 by the holder transferring device intermittently and a certain timing to pipette position a as described above. Structure and operation of the holder transferring device, being like those of known holder transferring devices, are not described herein.

The pipette device reciprocates the pipette p at a certain timing. The lowest position of the pipette p is controlled to be located slightly above the bottom of each vacuous blood gathering tube 3.

The top of the pipette p is connected with a tank 9 through a tube 8 as shown in FIG. 1. In the tube 8, a switching valve V is connected with an absorbing pump P. Accordingly, in the pipette p and the tube 8, wash water is filled in the usual condition, and by switching of the switching valve V and the absorbing pump P, a certain amount of blood in the vacuous blood gathering tube 3 is absorbed, and then the inside of the tube is washed.

Figure 2:
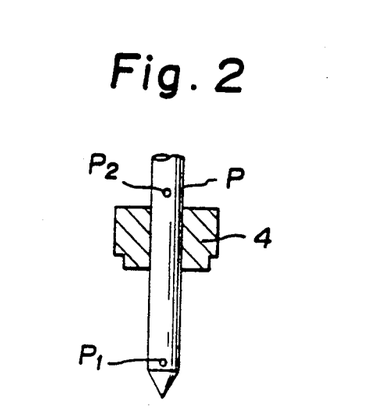
FIG. 2 is a side view to show the structure of a tip portion of a pipette.

As shown in FIG. 2, small holes p1 and p2 forming space to pass air are made on the tip portion of the pipette p. When the pipette p pierces the stopper 4 on the vacuous blood gathering tube 3, the small holes p1 and p2 pass air in the vacuous blood gathering tube 3, and a second stage of air releasing is done to any vacuum which remains by the first stage of air releasing by the vacuum breaking needle 10. Further, when blood is absorbed by the pipette p, a certain amount of blood is absorbed through the small holes p1 and p2 by soaking the small holes p1 and p2 in the blood.

The pipette holder 7 to hold the pipette p is set to be able to reciprocate by a pipette reciprocating device, and the vacuum breaking needle 10 is fixed at the pipette holder 7.

The distance D between the vacuum breaking needle 10 and the pipette p is set at the distance between axes b1 and b2 of three vacuous blood gathering tubes 3 held by the holder 30.

Figure 8:
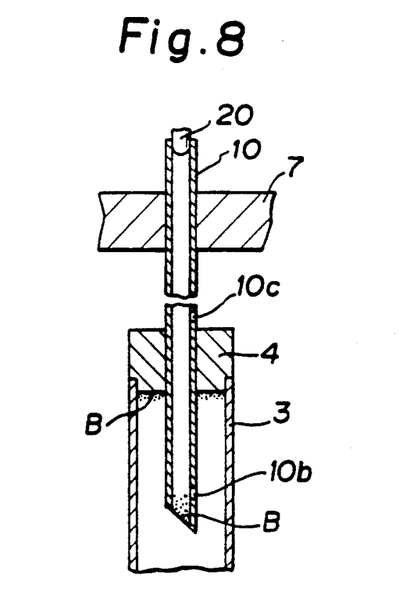
FIG. 8 is a partial sectional view to show the condition wherein the vacuum breaking needle penetrates the vacuous blood gathering tube.

As shown in FIG. 8, the vacuum breaking needle 10 is shaped like a pipe and made of metal or hard plastics etc. Both tips thereof are connected with air, and small holes 10b and 10c leaving a space to pass air are made on the tip portion. When the vacuum breaking needle pierces the stopper 4 on the vacuous blood gathering tube 3, the small holes 10b and 10c pass the air in the vacuous blood gathering tube 3, and the first stage of air releasing is done. At this time, the tip of the vacuum breaking needle is controlled to avoid contact with the blood.

The outside diameter of the inserting needle 20 to be inserted in an air passage of the vacuum breaking needle 10 is smaller than the inside diameter of the air passage of the vacuum breaking needle 10. The top portion thereof is fixed by a supporter 21 and the bottom portion 20a thereof is rounded.

Figure 7:
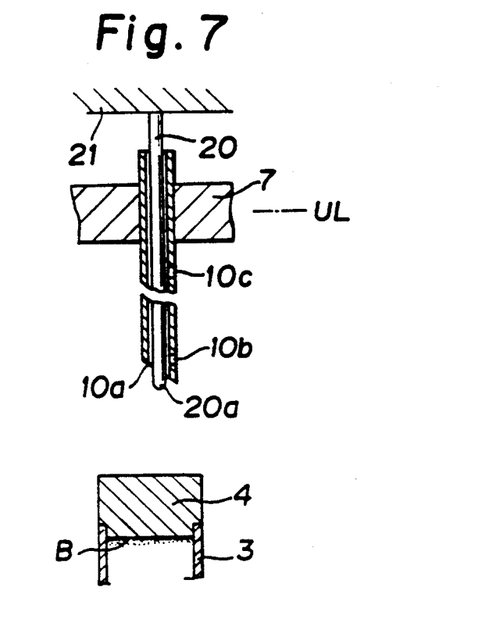
FIG. 7 is a sectional view to show the condition wherein the vacuum breaking needle is set at its highest position.

As shown in FIG. 7, the length of the inserting needle 20 is a little greater than the length of the vacuum breaking needle 10. When the vacuum breaking needle 10 rises to the highest position UL, the tip 20a of the inserting needle 20 appears below the tip 10a of the vacuum breaking needle 10.

As shown in FIG. 8, when the vacuum breaking needle 10 is at its lowest position, the inserting needle 20 has a length sufficient such that the tip 20a is inserted a little in the top portion of the vacuum breaking needle 10. Accordingly, the inserting needle 20 is prevented from coming out of the vacuum breaking needle 10.

When the pressure inside of the vacuous blood gathering tube 3 is made equal to the pressure of ambient air by the automatic medical sampling device A constructed as above, as the vacuous blood gathering tube 3 held by the holder 30 is transmitted directly under the vacuum breaking needle 10, the pipette holder 7 moves down, and the tip of the pipette p pierces the stopper 4 and enters the vacuous blood gathering tube 3. Blood in the vacuous blood gathering tube 3, having pressure equal to the pressure of air, directly under the pipette p, is absorbed.

The vacuum breaking needle 10, when the releasing of air is finished, and the pipette p, when the absorbing of blood is finished, rises to the highest position UL, by upward movement of the pipette holder 7. At this time, blood B, clinging in the air passage in the vacuum breaking needle 10, is pushed downward by the inserting needle 20, and the needle is prevented from being stopped up.

The second preferred embodiment will be explained in accordance with FIG. 3, FIG. 4, and FIG. 5. The automatic medical sampling device A in this preferred embodiment comprises holder 30 to position vacuous blood gathering tubes therein, an axis 31 on which to rotate the holder 30 from the blood gathering tube inserting position b to the blood absorbing position c, pipette p to absorb blood from the vacuous blood gathering tube 3 at the blood absorbing position c, vacuum breaking needle 10 near the pipette p to insert air in the tube 3, a reciprocating device 40 to move the pipette p and the vacuum breaking needle 10, inserting needle 20 inserted in the vacuum breaking needle 10, and washing device 50 to wash the pipette p after finishing absorbing of blood.

The vacuous blood gathering tube 3 is made as usual. The stopper 4 is set on the top portion thereof and seals up the tube 3.

Figure 5:
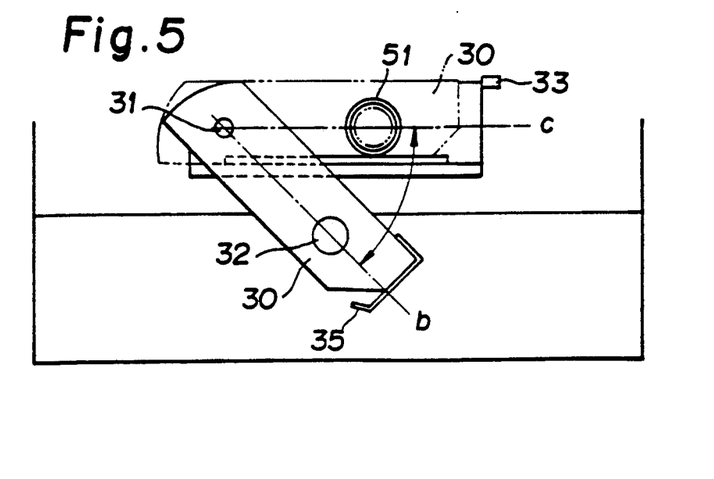
FIG. 5 is a plan view to show the blood gathering tube holder portion of the automatic medical sampling device in the second preferred embodiment.
Figure 6:
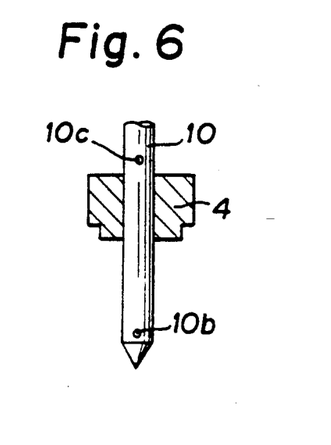
FIG. 6 is a side view to show structure of a tip portion of the vacuum breaking needle.

As shown in FIG. 5, the holder 30 to support the vacuous blood gathering tube 3 comprises the axis 31 on which to hold and rotate the holder 30, a supporting hole 32 to support one vacuous blood gathering tube 3, and a sensor 33 to detect whether the holder 30 is positioned at a certain blood absorbing position c. The reference numeral 35 in the figure denotes a handle.

The sensor 33 detects whether the holder 30 is set exactly at a certain blood absorbing position c. In the case where the holder 30 is not set exactly at the certain blood absorbing position c, reciprocation of the pipette p is stopped, and if the pipette p is operated, the operation is stopped immediately. In this case, resetting of the pipette p is done by turning ON of an INT switch 34 shown in FIG. 3. The INT switch 34 also can set to the initial condition of the automatic medical sampling device A in this preferred embodiment.

The pipette p reciprocates under control of reciprocating device 40. The lowest position of the pipette p is controlled by a sensor 41 to be located at a position slightly above the bottom of the vacuous blood gathering tube 3.

The top of the pipette p is connected with a tank in the wasing device 50 (not shown in the figure). Wash water is supplied in the tank by the switching valve, and washing inside the tank is carried out. At this time, wash water, after washing, is drained to a washing means 51 which appears when the holder 30 is rotated to the blood gathering tube inserting position b (shown in FIG. 5).

Figure 3:
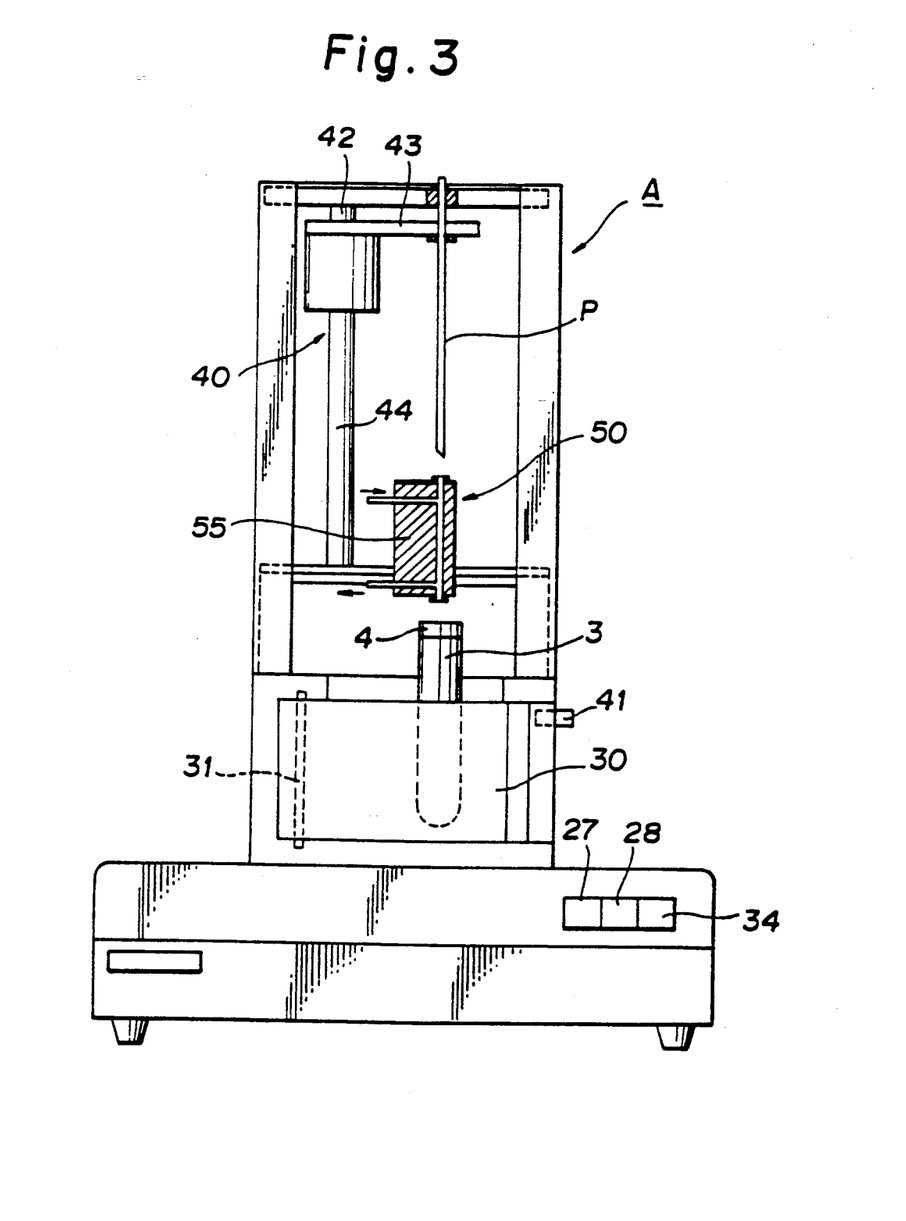
FIG. 3 is a front view to show a whole structure of the automatic medical sampling device to explain a second preferred embodiment of the invention.

As shown in FIG. 3, the reciprocating device 40 comprises sensor 41, sensor 42 set at the highest position of the pipette p, an arm 43 to hold the pipette p and the vacuum breaking needle 10, a rail 44, and a driving device (not shown) to make the arm 43 reciprocate along the rail 44.

The vacuum breaking needle 10 is shaped like a pipe and made of metal or hard plastics, etc. As shown in FIG. 4, the top portion thereof is fixed on the bottom surface of the arm 43, and small holes 10b and 10c, leaving a space to pass air, are formed on the tip portion. When the vacuum breaking needle 10 pierces the stopper 4 on the vacuous blood gathering tube 3, small holes 10b and 10c pass air in the vacuous blood gathering tube 3, and air is released from the vacuous blood gathering tube 3. At this time, the reciprocating device 40 is controlled to avoid contacting the tip of the vacuum breaking needle 10 with blood.

The outside diameter of the inserting needle 20 to be inserted in the, air passage in the vacuum breaking needle 10 is smaller than the inside diameter of the air passage in the vacuum breaking needle 10. The top portion thereof is inserted in a hole 45 in the arm 43, the tip thereof is fixed at the supporter 21 at the automatic medical sampling device A, and the bottom portion 20a thereof is rounded.

The length of the inserting needle 20 is a little greater than the length of the vacuum breaking needle 10. When the vacuum breaking needle rises to the highest position UL, the tip 20a of the inserting needle 20 appears below the tip 10a of the vacuum breaking needle 10, as shown in FIG. 7.

As shown in FIG. 8, when the vacuum breaking needle 10 falls to the lowest position, the inserting needle 20 has a length sufficient to maintain the tip 20a inserted slightly in the top portion of the vacuum breaking needle 10. Accordingly, the inserting needle 20 is prevented from extending out of the vacuum breaking needle 10.

The washing device 50 comprises a washing unit to wash the inside of the pipette p and a washing unit to wash the outside of the pipette.

Figure 9:
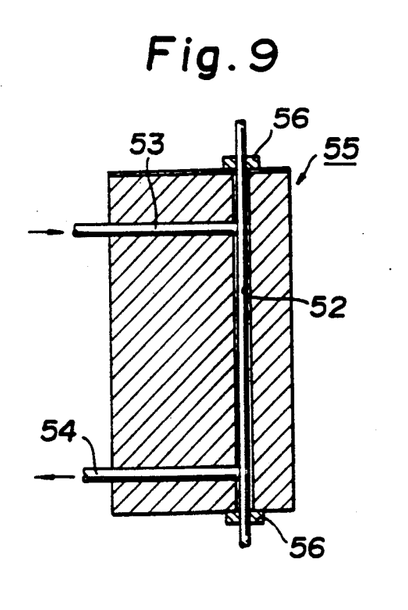
FIG. 9 is a sectional view of the wash block.

As shown in FIG. 3 and FIG. 9, the washing unit to wash the outside of the pipette p comprises a pipette inserting hole 52 to be inserted when the pipette p indexes up and down, a wash water supplying passage 53 connected with the pipette inserting hole 52, and a wash water draining passage 54 under the wash water supplying passage 53 and connected with the pipette inserting hole 52. The pipette inserting passage 52, the wash water supplying passage 52, and the wash water draining passage 54 are located in a washing block 55.

As shown in FIG. 9, O-rings 56 are at the tip portions of the pipette inserting passage 52. The O-rings 56 allow the pipette p to move and prevent wash water in the pipette inserting passage 52 from leaking outside the washing block 55.

Accordingly, wash water enters from the tank set outside of the automatic medical sampling device A to the pipette inserting hole 52 through the wash water supplying passage 53. While the pipette p, which finishes absorbing blood, rises through the pipette inserting hole 52, the outside of the pipette p is washed and wash water polluted thereby is directed outside the automatic medical sampling device A. Washing can be done while the pipette p is stopped temporarily in the pipette inserting hole 52.

Figure 4:
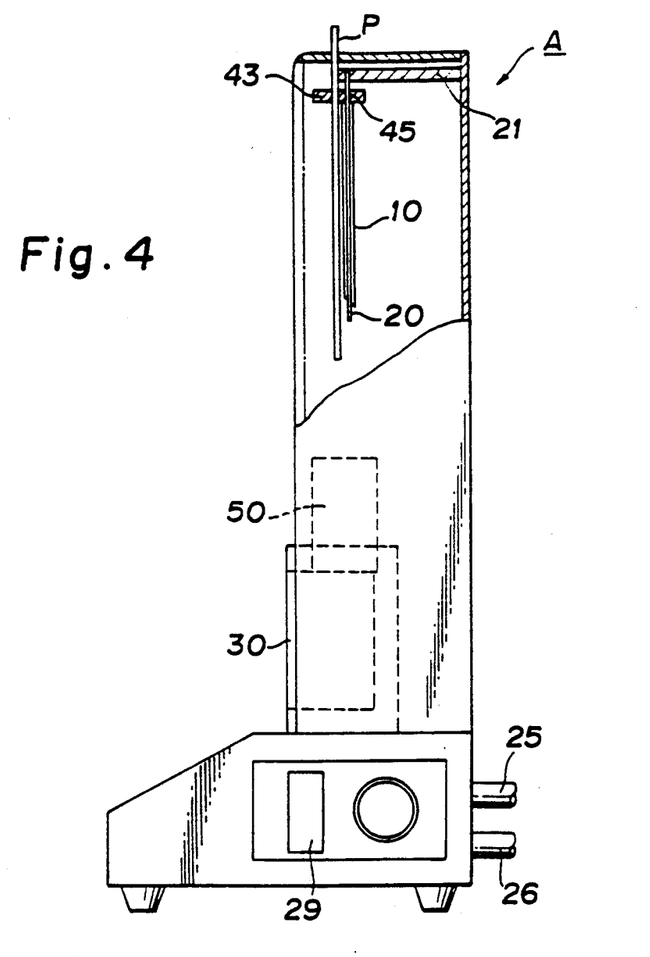
FIG. 4 is a side view of the automatic medical sampling device in the second preferred embodiment.

In FIG. 4, reference numeral 25 denotes a signal cable, reference numeral 26 denotes a power cable, and reference numeral 29 denotes a power switch. In FIG. 3, reference numeral 27 denotes a starting switch, and reference numeral 28 denotes a stopping switch.

The case where blood in the vacuous blood gathering tube 3 is absorbed by the automatic medical sampling device A will be explained as follows.

The holder 30 is pushed forward by the fulcrum of the axis 31 and set at the blood gathering tube inserting position b. After one vacuous blood gathering tube 3 is placed in a supporting hole 32 in the holder 30, the holder 30 is set at the blood absorbing position c. At this time, sensor 33 detects whether the holder is set at a certain position. If the holder is set at the certain position, determined by a detection signal sent to the reciprocating device 40, the pipette p and the vacuum breaking needle 10 fall to the lowest position, and the stopper 4 on the vacuous blood gathering tube 3 is pierced. At this time, the pipette p is soaked with blood in the vacuous blood gathering tube 3, and the small holes 10a and 10b of the vacuum breaking needle 10 pass air in the vacuous blood gathering tube to release air therein.

The vacuum breaking needle 10, which finishes absorbing blood rises to the highest position UL by upward movement of the arm 43. Any blood clinging inside and outside the pipette p is washed in the washing device 50 as above, and blood clinging inside the air passage in the vacuum breaking needle 10 is directed downward by the inserting needle 20 so that needle 10 is prevented from being stopped up.

Each operation of absorbing, vacuum breaking, and clearing can also be done manually by setting a manual switch and a manual switch for controlling the movement of the pipette p.

Figure 10:
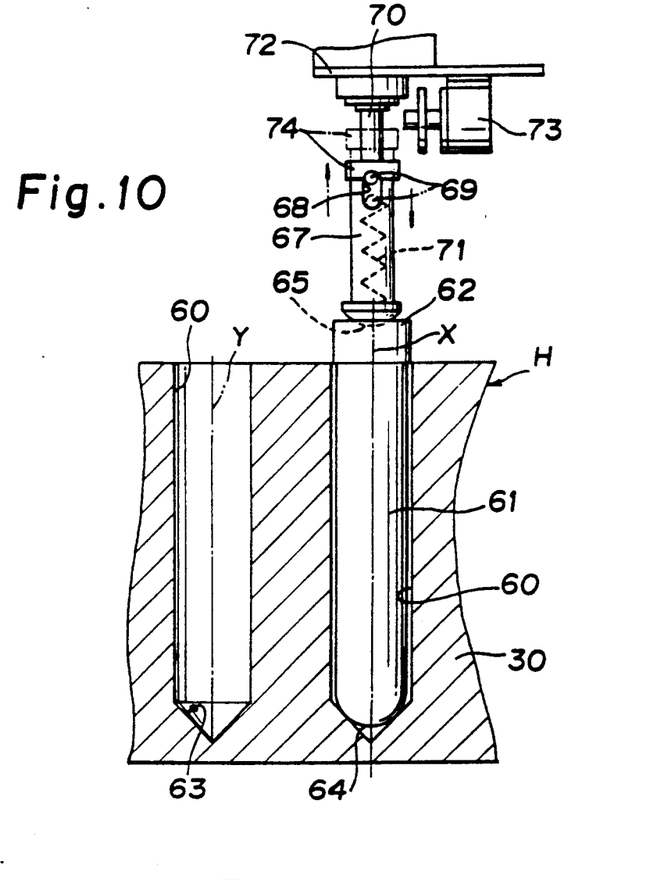
FIG. 10 is schematic view to show a whole structure of the container holder provided in the invention and the stirring device to rotate the container and stir blood in the container holder.

The container holder will now be explained in accordance with FIG. 10. The holder H comprises the container holder 30, and plural receiving holes 60 set at a certain interval at a certain portion in the container holder 30. A container 61, such as a test tube or a blood gathering tube, is located in the receiving holes 60.

The receiving holes 60 have a depth sufficient to receive the container 61, except a rubber stopper thereon, and the bottom of each hole has slope 63 v-shaped in cross-section. Accordingly, when a container 61 is set in a receiving hole 60, the bottom 64 of the container 61 is fixed by the slope 63, and the axis X of the container 61 is set automatically to coincide with the axis Y of the receiving hole 60.

In this case, in the top portion of the container 61, an indented portion 65 on the top portion of the rubber stopper 62 is fixed on the bottom portion of the stirring bar 67. Accordingly, the container 61 is positioned vertically according to the axis Y of the receiving holes 60.

Figure 11:
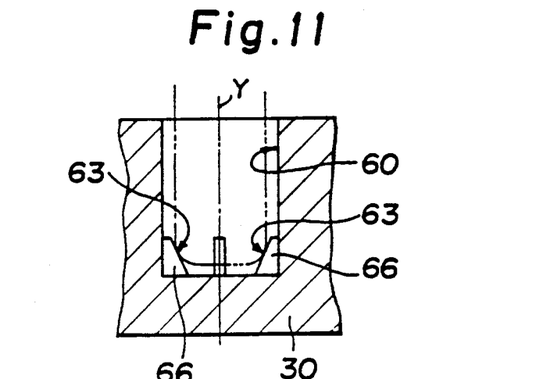
FIG. 11 is a sectional view to show another example of the container holder.

The slope angle of the slope 63 is not limited to the angle in the preferred embodiment shown in the figure. Broader or narrower angles, than the angle in the preferred embodiment shown in the figure can be used according to the shape of the bottom of the container 61 used. Alternatively, as shown in FIG. 11 projections 66 having slope 63 can be set at a certain interval on the bottom of the receiving holes 60, indented in cross-section.

How a container 61 is positioned in a receiving hole 60 in the holder H constructed as above and is rotated and stirred by the stirring device will be explained as follows.

Any stirring device of a known non-contact rotating type can be used. One example thereof will now be explained in accordance with FIG. 10. The stirring device comprises a stirring bar 67 to be pushed on the top of the container 61 sample of blood etc. therein, an elongated groove 68 in the top portion of the stirring bar 67, a motor axis 70 for stirring and having a projection 69 for reciprocation in the elongated groove 68, a motor (not shown) for rotating the stirring bar to rotate the motor axis 70 for stirring, a coil spring 71 to normally push the stirring bar 67 downward, a holder 72 to hold the motor for rotating the stirring bar and the stirring bar 67, a stirring bar reciprocation device (not shown) to make the holder 72 reciprocate, and a position sensor 73 set in the holder 72 to control rotation of the stirring bar 67.

The bottom portion of the stirring bar 67 is shaped to be pushed tightly on the indented portion in the top of the rubber stopper 62. The coil spring 71 is set in a barrel-shaped body located in the bottom portion thereof. The elongated groove 68 is located in the top portion of the barrel-shaped body.

The top portion of the motor axis 70 for stirring is connected with the motor for rotating the stirring bar (not shown), and the bottom portion thereof has the projection 69 for reciprocation in the elongated groove 68. The top portion of the coil spring 71 is fixed at the bottom portion of the motor axis 70 for stirring, and accordingly, the coil spring 71 normally pushes the stirring bar 67 downward.

Position sensor 73, located near the stirring bar 67 and in the holder 72, comprises a known reflecting light sensor to detect the position of the top portion of the stirring bar 67 moving downward by the stirring bar reciprocating device to stop driving thereof.

Accordingly, when a container 61 in the holder H is rotated and stirred by the stirring device, the holder 72 for the stirring bar 67 is made to move downward by the stirring bar reciprocating device, and the bottom portion of the stirring bar 67 is pushed against the rubber stopper 62 on the container 61.

At this time, the holder 72 has not yet reached the lowest position and continues to fall. However, since the stirring bar 67 is being pushed against the rubber stopper 62 on the container 61, further downward movement of the holder 72 after pushing is prevented. As a result, the projection 69 in the motor axis 70 for stirring resists the force of the coil spring 71 and falls along the elongated groove 68 in the stirring bar 67. Accordingly, the position sensor 73 also moves downward with the holder 72, and at a certain position the position sensor 73 detects the position of the top portion 74 of the stirring bar 67.

After the position sensor 73 detects the position of the top portion of the stirring bar 67 as above, the position sensor 73 sends a detection signal to a motor to make the holder reciprocate or to a controlling device (not shown) to stirring bar reciprocating device is stopped, pushing pressure is maintained in the condition that the stirring bar 67 is pushed against the container 61, and the axis X of the container 61 is set to coincide with the axis Y of the receiving holes 60.

Thereafter, the motor for rotating the stirring bar operates, the container 61 is rotated, and a sample in the container 61 is rotated and stirred.

After stirring is finished, the control device operates and rotates the motor in a manner to make the holder reciprocate, and thereby the holder 72 starts to rise. Accordingly, the position sensor 73 and the motor axis 70 for stirring rise. At this time, since the stirring bar 67 is pushed downward by the coil spring 71, force of the spring against the rubber stopper 62 of the container 61 is maintained.

After the position sensor 73 and the motor axis 70 for stirring rise as above, the projection 69 is in contact with the top portion of the long groove 68, since the projection 69 rises in contact with the stirring bar 67. After the bottom portion of the stirring bar 67 separates from the rubber stopper 62 on the container 61 and returns to its former position, operation of the motor to reciprocate the holder is stopped.

Accordingly, in the holder H in this preferred embodiment, since the axis X of the container 61 is set to coincide with the axis Y of the receiving holes 60, strange sounds do not occur, stirring can reliably be obtained, and any bar code information on the container 61 can be read reliably by a bar code reading device during rotation of the container 61 and stirring.

Figure 12:
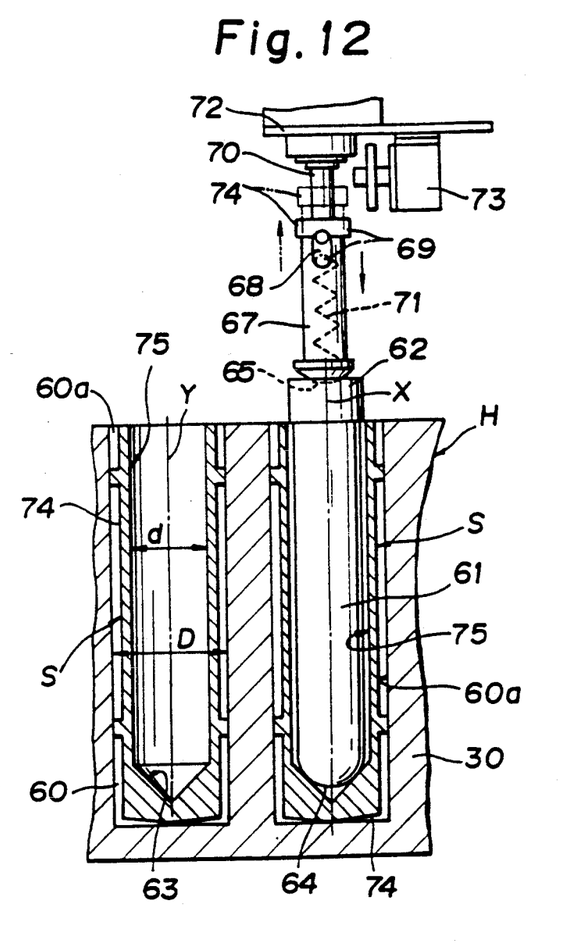
FIG. 12 is a view to show a whole structure of the container maintainer provided in the invention, and the stirring device to rotate the container and stir blood in the container maintainer.

The container maintainer in the invention now will be explained in accordance with FIG. 12. The holder H comprises container holder 30, and plural receiving holes 60 at a certain interval at a certain portion in the container holder 30 and indented in cross-section. The container 61 held in the container maintainer S is positioned in the receiving holes 60.

The container maintainer S comprises a body 74 having an outside diameter D contacting the inside of the receiving holes 60, and retaining holes 75 to position the container 61 along the axis Y of the receiving holes 60.

The retaining holes 75 have a depth sufficient to retain the portion of the container 61 except the rubber stopper 62 thereon. The inside diameter d of each hole 75 is slightly greater than the outside diameter of the container 61 so as not to disturb rotation thereof, and the bottom of the hole has slope 63 v-shaped in cross-section.

Accordingly, in the case where a container 61 is set in a retaining hole 75, the bottom 64 of the container 61 is fixed by the slope 63, and the axis X of the container 61 is set automatically to coincide with the axis Y of the retaining hole 75 and a receiving hole 60.

In this case, the indented portion 65 on the top portion of the rubber stopper 62 on container 61 is fixed on the bottom portion of the stirring bar 67. Accordingly, the container 61 is positioned vertically according to the axis Y of the retaining holes 75.

Figure 13:
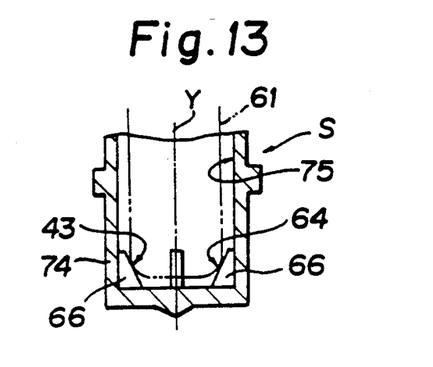
FIG. 13 is a sectional view to show another example of the container maintainer.

A slope angle of the slope 63 is not limited to the angle in the preferred embodiment shown in the figure. Broader or narrower angles than the angle in, the preferred embodiment shown in the figure can be used according to the shape of the bottom of the used container 61. Alternatively, as shown in FIG. 13, the projections 66 having the slope 63 can be set at a certain interval in the bottom of the retaining holes 75 indented in cross-section.

How the container 61 is set in the retaining holes 75 in the container maintainer S constructed as above, and the container maintainer S is positioned in a receiving holes 60 in the holder H, rotated, and stirred by the stirring device as explained above, will be explained shortly.

By the explained construction, after the position sensor 73 detects the position of the top portion of the stirring bar 67, the position sensor 73 sends a detection signal to the motor to make the holder reciprocate or to the controlling device (not shown) to control driving of each motor. Accordingly, the operation of the stirring bar reciprocating device is stopped, the pressure is maintained in the condition that the stirring bar 67 is pushed on the container 61, and the axis X of the container 61 is set to coincide with the axis Y of the retaining holes 75 and the receiving holes 60.

In the container maintainer S in this preferred embodiment, since the axis X of the container 61 is set to coincide with the axis Y of the retaining holes 75 and the receiving holes 60, strange sounds do not occur, stirring can reliably be obtained, and any bar code information on the container 61 can be read reliably by a bar code reading device during rotation of the container 61 and stirring.

Figure 14:
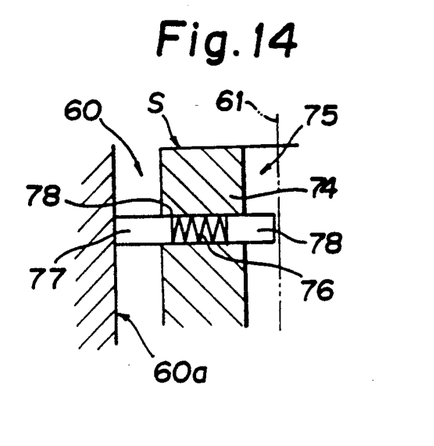
FIG. 14 is an enlarged sectional view to show another example of structure of the upper portion of the container maintainer.

In this invention, as shown in FIG. 14, small holes 76 are set horizontally on the top of the container maintainer S, projections 77 and 78 are set to move freely in the small holes 76 by a spring 79 in the small holes 76, projection 77 is moved into the receiving holes 60, projection 78 is moved into the retaining holes 75, the container 61 positioned in the retaining holes 75 is held more securely by the projection 77, and the container maintainer S is held more securely by the projection 78.

The stirring device in the automatic medical sampling device will now be explained in accordance with FIG. 15. The stirring device comprises the stirring bar 67 to be impressed on the top portion of the container, elongated groove 68 at the top portion of the stirring bar 67, the motor axis 70 for stirring having a projection 66 to reciprocate in the elongated groove 68, and a motor for rotating the stirring bar 81 for stirring 70. A coil spring 71 normally pushes the stirring bar 67 downward, a holder 72 holds the motor for rotating the stirring bars 81 and 67, a stirring bar reciprocating device 82 reciprocates the holder 72, and position sensor 73 in the holder 72 controls rotation of the stirring bar 67.

Figure 15:
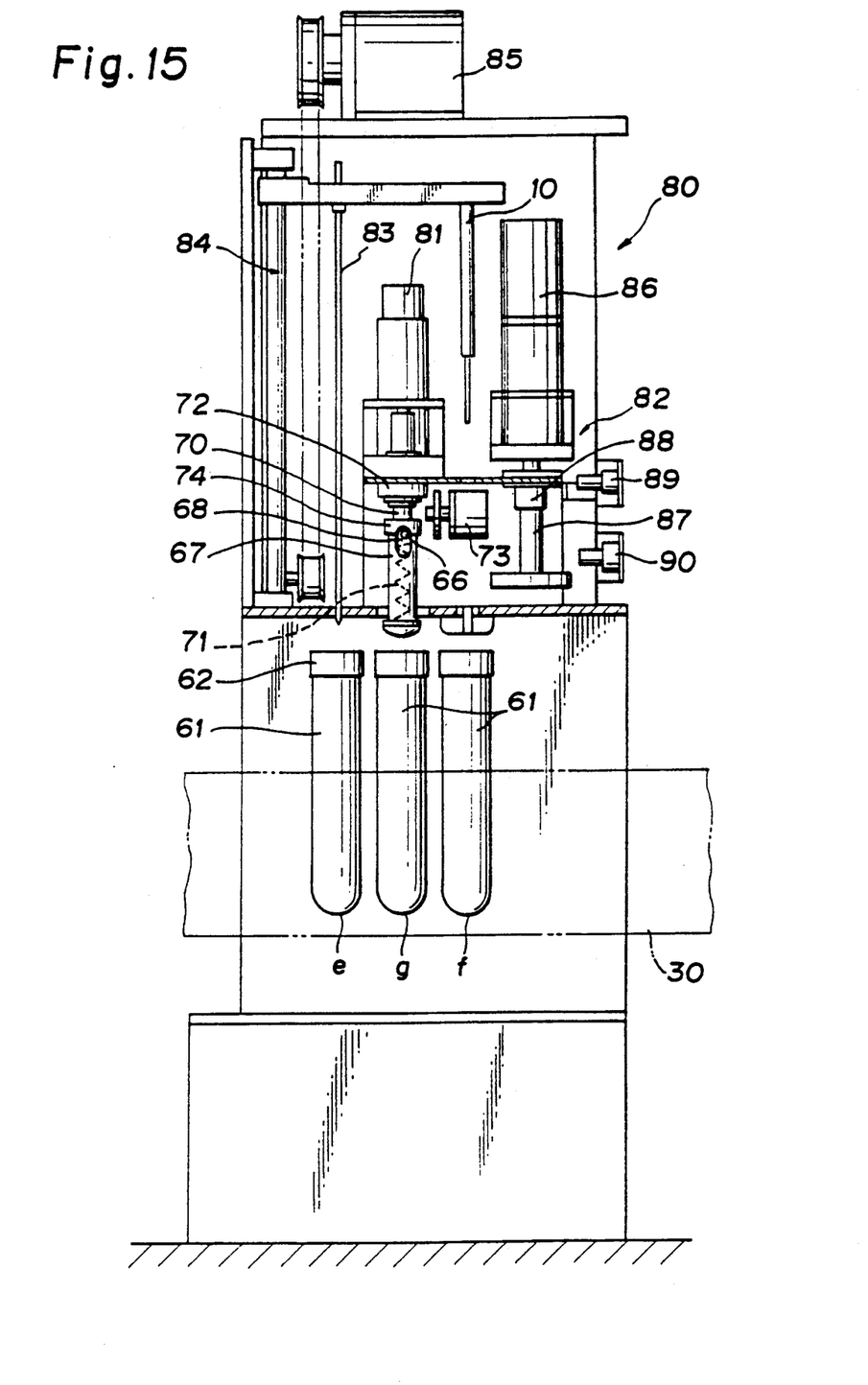
FIG. 15 is a view to show a whole structure of the stirring device provided in the invention.

In FIG. 15, reference numeral 83 denotes an absorbing tube to absorb a sample at the sample absorbing position e. Reference numeral 84 denotes a reciprocating device to guide the absorbing tube 83. Reference numeral 85 denotes a motor for the reciprocating device 84. Reference numeral 10 denotes the vacuum breaking needle for equalizing the vacuum in the container 61 with air by being guided to the position f with the absorbing tube 83.

In the embodiment, a test tube is used as container 61, and the rubber stopper 62 is set on the top thereof. The container 61 is positioned in the container holder 30, and is transferred intermittently from the right side to the left side by one pitch in FIG. 15, and reaches the absorbing position e from the vacuum breaking position f through the stirring position g.

The bottom portion of the stirring bar 67 is shaped to be retained tightly in the indented portion in the top of the rubber stopper 62. The coil spring 71 is set in a barrel-shaped body in the bottom portion thereof. The elongated groove 68 is provided in the top portion of the barrel-shaped body.

The top portion of the motor axis 70 for stirring is connected with the motor 81 for rotating the stirring bar, and the bottom portion thereof has projection 66 for reciprocation in the elongated groove 68. The top portion of the coil spring 71 is fixed at the bottom portion of the motor axis 70 for stirring and, accordingly, the coil spring 71 normally pushes the stirring bar 67 downward.

The holder 72 holds the motor 81 for rotating the stirring bar and the stirring bar 67 at the tip portion of the left side in FIG. 15, and holds the stirring bar reciprocating device 82 at the tip portion of the right side.

The stirring bar reciprocating device 82 comprises a motor 86 to reciprocate the holder and a connector 88 to connect with a rotation axis 87 of the motor 86. The connector 88 is fixed at the holder 72.

The surface of the rotation axis 87 of the motor 86 to reciprocate the holder has a male screw groove which coincides with a female screw (not shown in the figure) set on the inside of the tube hole (not shown) of the connector 88. Accordingly, the holder 72 reciprocates by rotating the rotation axis 87 of the motor 86 to make the holder reciprocate. As shown in FIG. 15, in this preferred embodiment, an upper limit switch 89 and a lower limit switch 90 are set near the holder 72, so that the highest position and the lowest position of the holder are determined. The upper limit switch 89 and the lower limit switch 90 can, for example, be made of a limit switch or light, sensor, etc.

The position sensor 73 is located near the stirring bar 67 and set in the holder 72, and comprises a known reflecting light sensor to detect the position of the top portion of the stirring bar 67 to move downward by the stirring bar reciprocating device 82 to stop driving thereof. A limit switch or a light sensor etc. of different constructions can be used.

Figure 16:
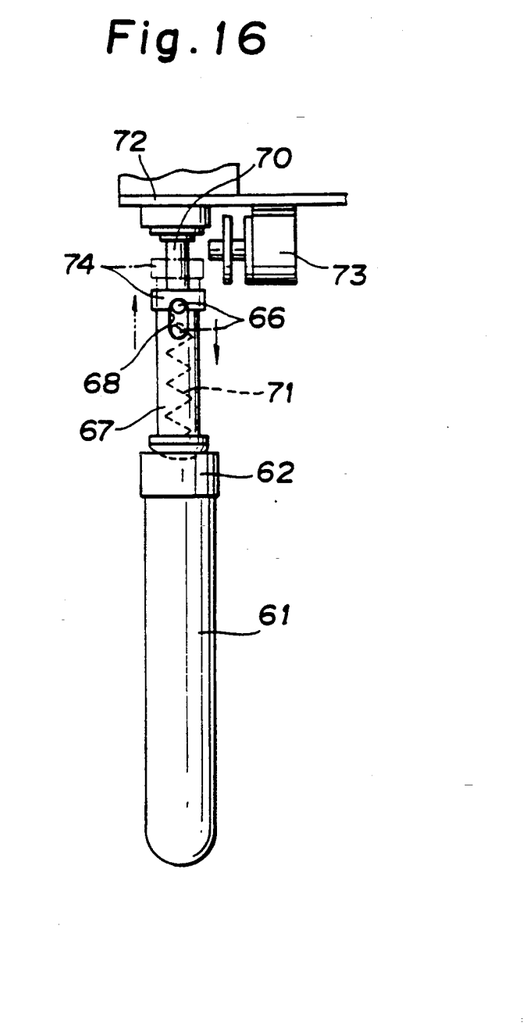
FIG. 16 is a view to show the operation of the main portion of the stirring device.

The operation for stirring the container 61 by the stirring device 80 in accordance with FIG. 16 will now be described as follows.

After the holder 72 for the stirring bar 67 falls by the stirring bar reciprocating device 82 and the bottom portion of the stirring bar 67 is pushed against the rubber stopper 62 on the container 61, the holder 72 has not yet reached the lowest position and continues to fall. However, since the stirring bar 67 is being pushed against the rubber stopper 62 on the container 61, further falling of the holder 72 is prevented. As a result, the projection 66 in the motor axis 70 for stirring resists the force of the coil spring 71 and moves downward along the groove 68 in the stirring bar 67. Accordingly, the pressure sensor 73 also moves downward with the holder 72, and at a certain position the position sensor 73 detects the position of the top portion 74 of the stirring bar 67.

After the position sensor 73 detects the position of the top portion of the stirring device 67 as above, the pressure sensor 73 sends the detection signal to the motor 86 to make the holder reciprocate or to a controlling device (not shown) to control driving of each motor. Accordingly, the operation of the stirring bar reciprocating device 82 is stopped, and the pushing pressure is maintained such that stirring bar 67 is pressed on the container 61 properly.

Thereafter, the motor 81 for rotating the stirring bar operates, the container 61 is rotated, and a sample in the container is rotated and stirred.

Following stirring, the control device operates to rotate the motor in a manner to make the holder reciprocate, and thereby the holder 72 starts to rise. In response, the pressure sensor 73 and the motor axis for stirring 70 also rise. At this time, since the stirring bar 67 is pushed downward by the force of coil spring 71, the rubber stopper 62 is maintained pressed on the container 61.

After the position sensor 73 and the motor axis 70 for stirring rise as above, and the projection 66 is in contact with the top portion of the groove 68 with the projection 66 in contact with the stirring bar 67 separated from the rubber stopper 62 on the container 61 and returned to its former position, operation of the motor 86 to make the holder reciprocate is stopped.

In the above embodiment, the operation of the motor to make the holder reciprocate is controlled by the pressure sensor. However, this invention is not limited to the above example. For example, the same effect can be obtained by using a limit switch. In the above example, the top portion of the stirring bar is detected by the pressure sensor. However the bottom portion or the other portion can be detected.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A stirring apparatus comprising:
   a stirring bar having a body circumscribing a cavity and an end portion covering said cavity, said end portion to be pushed onto contact with a top portion of a container;
   an elongated groove set in a top portion of said body of said stirring bar;
   a spindle having a projection in one end, said projection contacting said stirring bar and set to reciprocate freely in said elongated groove;
   a motor attached to another end of said spindle for rotating said spindle and said stirring bar for rotating said container when in contact with said stirring bar;
   a spring positioned within said cavity of said stirring bar, said spring having a top end fixed to said one end of said spindle and a bottom end contacting said end portion of said stirring bar for normally pushing said stirring bar downward;
   a holder for holding said motor; and
   stirring bar operating means for reciprocating said holder and controlling operation of said motor; wherein
   said stirring bar operating means includes a position sensor means in said holder for indicating a position of a top portion of said stirring bar, and controls reciprocating said holder in response to the sensed position of said stirring bar.

2. An automatic medical sampling device comprising:
   a tube holder for positioning a plurality of vacuous liquid gathering tubes therein;
   a vacuum breaking needle to reciprocally engage each vacuous liquid gathering tube;
   a pipette for absorbing a liquid from each vacuous liquid gathering tube at an absorbing position; and
   stirring means positioned between said vacuum breaking needle and said pipette for stirring each liquid gathering tube, wherein
   said stirring means includes:
   a stirring bar having a body circumscribing a cavity and an end portion covering said cavity, said end portion to be pushed onto contact with a top portion of each vacuous liquid gathering tube;
   an elongated groove set in a top portion of said body of said stirring bar;
   a spindle having a projection in one end, said projection contacting said stirring bar and set to reciprocate freely in said elongated groove;
   a motor attached to another end of said spindle for rotating said spindle and said stirring bar for rotating said tube when in contact with said stirring bar;
   a spring positioned within said cavity of said stirring bar, said spring having a top end fixed to said one end of said spindle and a bottom end contacting said end portion of said stirring bar for normally pushing said stirring bar downward;
   a holder for holding said motor; and
   stirring bar operating means for reciprocating said holder and controlling operation of said motor; wherein
   said stirring bar operating means includes a position sensor means in said holder for indicating a position of a top portion of said stirring bar, and controls reciprocating said holder in response to the sensed position of said stirring bar.

* * * * *